(12) United States Patent
Lagree

(10) Patent No.: US 11,826,614 B2
(45) Date of Patent: *Nov. 28, 2023

(54) BIOELECTRICAL SIGNAL CONTROLLED EXERCISE MACHINE SYSTEM

(71) Applicant: Lagree Technologies, Inc., Chatsworth, CA (US)

(72) Inventor: Sebastien Anthony Louis Lagree, Chatsworth, CA (US)

(73) Assignee: Lagree Technologies, Inc., Chatsworth, CA (US)

( * ) Notice: Subject to any disclaimer, the term of this patent is extended or adjusted under 35 U.S.C. 154(b) by 52 days.

This patent is subject to a terminal disclaimer.

(21) Appl. No.: 17/952,822

(22) Filed: Sep. 26, 2022

(65) Prior Publication Data

US 2023/0012546 A1    Jan. 19, 2023

Related U.S. Application Data

(63) Continuation of application No. 17/062,778, filed on Oct. 5, 2020, now Pat. No. 11,458,365, which is a
(Continued)

(51) Int. Cl.
*A63B 24/00* (2006.01)
*A61B 5/375* (2021.01)
(Continued)

(52) U.S. Cl.
CPC ........ *A63B 24/0087* (2013.01); *A61B 5/0006* (2013.01); *A61B 5/375* (2021.01);
(Continued)

(58) Field of Classification Search
None
See application file for complete search history.

(56) References Cited

U.S. PATENT DOCUMENTS

| 1,621,477 A | 3/1927 | Pilates |
| 3,770,267 A | 11/1973 | McCarthy |

(Continued)

FOREIGN PATENT DOCUMENTS

| WO | 2004096376 A1 | 11/2004 |
| WO | 2014084742 A1 | 6/2014 |

OTHER PUBLICATIONS http://tera.lunar-europe.com; TERA Fitness Mat; Lunar Europe; Jun. 8, 2014.

(Continued)

*Primary Examiner* — Shila Jalalzadeh Abyaneh
(74) *Attorney, Agent, or Firm* — Neustel Law Offices

(57) ABSTRACT

A bioelectrical signal controlled exercise machine system for allowing an exerciser to control the state of an exercise machine and exercise environment. The bioelectrical signal controlled exercise machine system generally includes an exercise machine, a bioelectrical sensor device and a control unit in communication with the bioelectrical sensor device and the exercise machine. The control unit is adapted to receive data from the bioelectrical sensor device relating to measured bioelectrical signals of the human exerciser, and wherein the control unit transmits a control signal to the exercise machine to change the state of the exercise machine based on the data from the bioelectrical sensor device.

20 Claims, 14 Drawing Sheets

Related U.S. Application Data continuation of application No. 15/181,377, filed on Jun. 13, 2016, now Pat. No. 10,792,538.

(60) Provisional application No. 62/174,649, filed on Jun. 12, 2015.

(51) Int. Cl.
*A61B 5/389* (2021.01)
*A61B 5/00* (2006.01)

(52) U.S. Cl.
CPC .......... *A61B 5/389* (2021.01); *A63B 2230/10* (2013.01); *A63B 2230/105* (2013.01)

(56) References Cited

U.S. PATENT DOCUMENTS

| | | | |
|---|---|---|---|
| 4,013,068 A | 3/1977 | Settle | |
| 4,759,540 A | 7/1988 | Yu | |
| 4,798,378 A | 1/1989 | Jones | |
| 4,949,726 A * | 8/1990 | Hartzell | A61B 5/38 273/460 |
| 5,066,005 A | 11/1991 | Luecke | |
| 5,201,694 A | 4/1993 | Zappel | |
| 5,263,913 A | 11/1993 | Boren | |
| 5,365,934 A | 11/1994 | Leon | |
| D362,700 S | 9/1995 | Breibart | |
| D382,319 S | 8/1997 | Gerschefske | |
| 5,681,249 A | 10/1997 | Endelman | |
| 5,738,104 A | 4/1998 | Lo | |
| 5,812,978 A | 9/1998 | Nolan | |
| 5,885,197 A | 3/1999 | Barton | |
| 5,967,955 A | 10/1999 | Westfall | |
| 6,152,856 A | 11/2000 | Studor | |
| 6,179,753 B1 | 1/2001 | Barker | |
| 7,108,635 B2 | 9/2006 | Howlett-Campanella | |
| 7,163,500 B2 | 1/2007 | Endelman | |
| 7,192,387 B2 | 3/2007 | Mendel | |
| 7,448,986 B1 | 11/2008 | Porth | |
| 7,537,554 B2 | 5/2009 | Zhuang | |
| 7,803,095 B1 | 9/2010 | Lagree | |
| 7,914,420 B2 | 3/2011 | Daly | |
| 7,931,570 B2 | 4/2011 | Hoffman | |
| 7,967,728 B2 | 6/2011 | Zavadsky | |
| 8,249,714 B1 | 8/2012 | Hartman | |
| 8,287,434 B2 | 10/2012 | Zavadsky | |
| 8,303,470 B2 | 11/2012 | Stewart | |
| 8,585,554 B2 | 11/2013 | Shavit | |
| 8,641,585 B2 | 2/2014 | Lagree | |
| 8,812,075 B2 | 8/2014 | Nguyen | |
| 8,852,062 B2 | 10/2014 | Dorsay | |
| 8,911,328 B2 | 12/2014 | Alessandri | |
| 9,011,291 B2 | 4/2015 | Birrell | |
| 9,199,123 B2 | 12/2015 | Solow | |
| 9,468,788 B2 * | 10/2016 | Bissu | A63B 21/00072 |
| 10,046,193 B1 | 8/2018 | Aronson | |
| 2001/0056011 A1 | 12/2001 | Endelman | |
| 2002/0137607 A1 | 9/2002 | Endelman | |
| 2002/0188216 A1 | 12/2002 | Kayyali | |
| 2003/0119635 A1 | 6/2003 | Arbuckle | |
| 2004/0214693 A1 | 10/2004 | Piaget | |
| 2005/0130810 A1 | 6/2005 | Sands | |
| 2005/0164856 A1 | 7/2005 | Parmater | |
| 2005/0275416 A1 | 12/2005 | Hervieux | |
| 2006/0046914 A1 | 3/2006 | Endelman | |
| 2006/0057549 A1 * | 3/2006 | Prinzel, III | A63B 71/06 434/247 |
| 2006/0183606 A1 | 8/2006 | Parmater | |
| 2006/0199712 A1 | 9/2006 | Barnard | |
| 2007/0087921 A1 | 4/2007 | Graham | |
| 2007/0202992 A1 | 8/2007 | Grasshoff | |
| 2007/0224582 A1 | 9/2007 | Hayashino | |
| 2007/0270293 A1 | 11/2007 | Zhuang | |
| 2008/0001735 A1 | 1/2008 | Tran | |
| 2008/0051256 A1 | 2/2008 | Ashby | |
| 2008/0058174 A1 | 3/2008 | Barnard | |
| 2008/0070765 A1 | 3/2008 | Brown | |
| 2008/0139975 A1 | 6/2008 | Einav | |
| 2008/0242519 A1 | 10/2008 | Parmater | |
| 2008/0248935 A1 | 10/2008 | Solow | |
| 2009/0005698 A1 * | 1/2009 | Lin | A61B 5/375 600/545 |
| 2009/0270227 A1 | 10/2009 | Ashby | |
| 2009/0291805 A1 | 11/2009 | Blum | |
| 2009/0312152 A1 | 12/2009 | Kord | |
| 2010/0125026 A1 | 5/2010 | Zavadsky | |
| 2010/0227748 A1 | 9/2010 | Campanaro | |
| 2010/0267524 A1 | 10/2010 | Stewart | |
| 2010/0298102 A1 * | 11/2010 | Bosecker | A61H 1/0237 482/54 |
| 2011/0009249 A1 | 1/2011 | Campanaro | |
| 2011/0018233 A1 | 1/2011 | Senner | |
| 2011/0077127 A1 | 3/2011 | Ishii | |
| 2011/0143898 A1 | 6/2011 | Trees | |
| 2011/0152045 A1 | 6/2011 | Horne | |
| 2011/0166002 A1 | 7/2011 | Savsek | |
| 2011/0172069 A1 | 7/2011 | Gerschefske | |
| 2011/0184559 A1 | 7/2011 | Benabid | |
| 2012/0015334 A1 | 1/2012 | Hamilton | |
| 2012/0088634 A1 | 4/2012 | Heidecke | |
| 2012/0143020 A1 | 6/2012 | Bordoley | |
| 2012/0190505 A1 | 7/2012 | Shavit | |
| 2012/0202656 A1 | 8/2012 | Dorsay | |
| 2012/0228385 A1 | 9/2012 | DeLuca | |
| 2012/0237911 A1 | 9/2012 | Watterson | |
| 2012/0295771 A1 | 11/2012 | Lagree | |
| 2013/0012829 A1 * | 1/2013 | Jo | G06F 3/015 381/109 |
| 2013/0017935 A1 | 1/2013 | Endelman | |
| 2013/0072353 A1 | 3/2013 | Alessandri | |
| 2013/0196835 A1 | 8/2013 | Solow | |
| 2013/0210578 A1 | 8/2013 | Birrell | |
| 2013/0289889 A1 | 10/2013 | Yuen | |
| 2014/0011645 A1 | 1/2014 | Johnson | |
| 2014/0066257 A1 | 3/2014 | Shavit | |
| 2014/0100089 A1 | 4/2014 | Kermath | |
| 2014/0121076 A1 | 5/2014 | Lagree | |
| 2014/0121078 A1 | 5/2014 | Lagree | |
| 2014/0121079 A1 | 5/2014 | Lagree | |
| 2014/0141948 A1 | 5/2014 | Aronson | |
| 2014/0148715 A1 | 5/2014 | Alexander | |
| 2014/0213415 A1 | 7/2014 | Parker | |
| 2014/0276183 A1 | 9/2014 | Badower | |
| 2015/0012111 A1 | 1/2015 | Contreras-Vidal | |
| 2015/0024914 A1 | 1/2015 | Lagree | |
| 2015/0057127 A1 | 2/2015 | Lagree | |
| 2015/0065318 A1 | 3/2015 | Lagree | |
| 2015/0072841 A1 | 3/2015 | Lagree | |
| 2015/0105223 A1 | 4/2015 | Bissu | |
| 2015/0141204 A1 | 5/2015 | Lagree | |
| 2015/0217164 A1 | 8/2015 | Lagree | |
| 2015/0220523 A1 | 8/2015 | Lagree | |
| 2015/0246263 A1 | 9/2015 | Campanaro | |
| 2015/0297944 A1 | 10/2015 | Lagree | |
| 2015/0343250 A1 | 12/2015 | Lagree | |
| 2015/0360068 A1 | 12/2015 | Lagree | |
| 2015/0360083 A1 | 12/2015 | Lagree | |
| 2015/0360113 A1 | 12/2015 | Lagree | |
| 2015/0364058 A1 | 12/2015 | Lagree | |
| 2015/0364059 A1 | 12/2015 | Marks | |
| 2015/0367166 A1 | 12/2015 | Lagree | |
| 2016/0008657 A1 | 1/2016 | Lagree | |
| 2016/0059060 A1 | 3/2016 | Lagree | |
| 2016/0059061 A1 | 3/2016 | Lagree | |
| 2016/0096059 A1 | 4/2016 | Lagree | |
| 2016/0271452 A1 | 9/2016 | Lagree | |
| 2020/0222741 A1 | 7/2020 | Aronson | |

OTHER PUBLICATIONS https://www.youtube.com/watch?v=xj2xuGsB3yo; Screenshot of YouTube Video "Iphone free App (Dec. 16, 2010) Finger Balance"; tuuske; Dec. 16, 2010.

(56) References Cited

OTHER PUBLICATIONS

PCT International Search and Opinion for PCTUS2016022888; Received Jul. 25, 2016.
PCT Preliminary Report on Patentability from International Searching Authority for PCTUS2016022888; Received Sep. 28, 2017.
PCT International Search and Opinion for PCTUS2017041638; Received Sep. 28, 2017.
PCT Preliminary Report on Patentability from International Searching Authority for PCTUS2017041638; Received Jan. 24, 2019.
http://www.puzzlebox.io/brainstorms/; Puzzlebox Brainstorms Webpage Article; Jun. 13, 2016.
http://www.brainproducts.com/productdetails.php?id=63&tab=1; LiveAmp Overview; Received and Printed Jun. 14, 2016.
http://www.cognionics.com/index.php/products/hd-eeg-systems/72-channel-system; Cognionics HD-72 Overview; Received and Printed Jun. 14, 2016.
http://www.cognionics.com/index.php/products/hd-eeg-systems/quick-20-dry-headset; Cognionics Quick-20 Dry EEG Headset; Received and Printed Jun. 14, 2016.
http://www.cognionics.com/index.php/products/mini-systems/multi-position-dry-headband; Cognionics Multi-Position Dry EEG Headband; Received and Printed Jun. 14, 2016.
http://www.cognionics.com/index.php/products/mini-systems/dry-eeg-headband; Cognionics Dry EEG Headband; Received and Printed Jun. 14, 2016.
http://www.cognionics.com/index.php/products/hd-eeg-systems/mobile-eeg-cap; Cognionics Mobile—72 Wireless EEG System; Received and Printed Jun. 14, 2016.

* cited by examiner

110

| TYPICAL ELEMENTS COMPRISING AN EXERCISE ENVIRONMENT ||
|---|---|
| Element | Definition |
| Light | Illumination of the gym facility / Visual |
| Music | Programmed Sound / Audible |
| Force | Weight or Resistance setting of an Exercise apparatus |
| Attitude | Pitch and/or Roll of exercise surface relative to horizontal |
| Tempo | Pace of exercise / speed of repetitions |
| Routine | Types of exercises performed in a sequence |

FIG. 1c

| Rhythm | Freq (Hz) | Amp(μV) | EEG Signal Amplitude Relating to Physiological Changes |
|---|---|---|---|
| alpha | 8-13 | 20-200 | Amplitude is high eyes closed, relaxation, meditation |
| | | | Amplitude is low: increased mental focus, visual stimulation |
| beta | 13-30 | 5-10 | Amplitude is high: alert, attentive to external stimuli or exerts mental effort |
| | | | Amplitude is low: active movements, distracted from mental effort |
| delta | 1-5 | 20-200 | Amplitude is high: At the onset of sleep |
| | | | Increases as Alpha decreases during sleep |
| theta | 4-8 | 10 | Amplitude is high: Appears with deeper sleep (REM) |
| | | | Increases as Alpha decreases during sleep |
| gamma | 27-100 | 10-20 | Amplitude is high: during information processing, |
| | | | accessing memory, or attentive cognitive thinking. |

FIG. 2

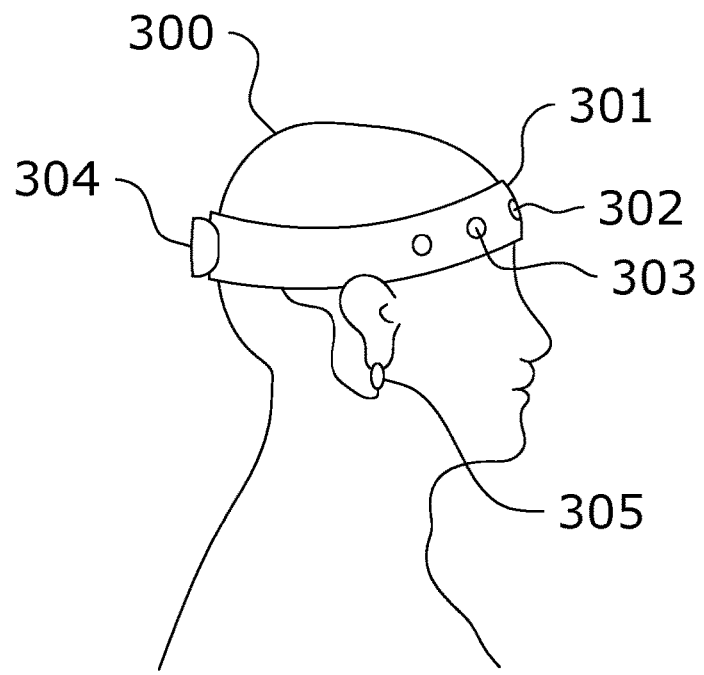

FIG. 3

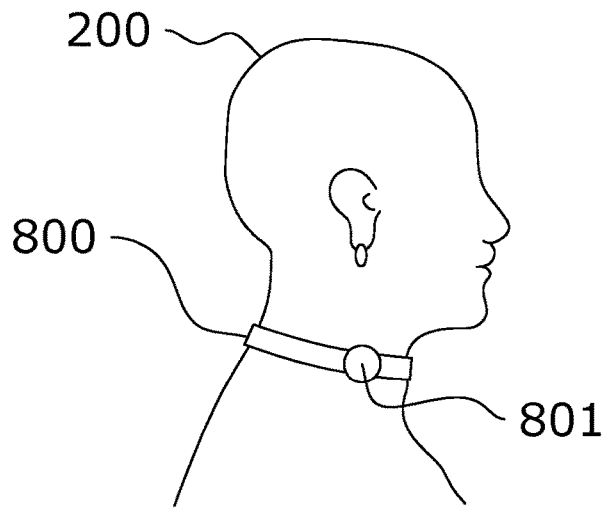

FIG. 8a

| VOICE COMMAND MENU | |
|---|---|
| WORD / PHRASE COMMAND | CONTROLLER FUNCTION |
| Up | Raises the ramp |
| Down | Lowers the ramp |
| Left | Rolls the Exercise Machine to the left |
| Right | Rolls the Exercise Machine to the right |
| Heavier (or "More") | Increases resistance one level |
| Lighter (or "Less") | Decreases resistance one level |
| Stop | Stops the roll or raise / lower when the exerciser wants it to stop |
| End | Ends the session, returns the Exercise Machine to starting Position |
| Louder | Increases volume of music or trainer's instructions |
| Softer | Decreases volume of music or trainer's instructions |
| *Other Words* | *Systems ONLY recognizes programmed words* |

FIG. 8b

BIOELECTRICAL SIGNAL CONTROLLED EXERCISE MACHINE SYSTEM

CROSS REFERENCE TO RELATED APPLICATIONS

The present application is a continuation of U.S. application Ser. No. 17/062,778 filed on Oct. 5, 2020 which issues as U.S. Pat. No. 11,458,365 on Oct. 4, 2022 which is a continuation of U.S. application Ser. No. 15/181,377 filed on Jun. 13, 2016 now issued as U.S. Pat. No. 10,792,538, which claims priority to U.S. Provisional Application No. 62/174,649 filed Jun. 12, 2015. Each of the aforementioned patent applications, and any applications related thereto, is herein incorporated by reference in their entirety.

STATEMENT REGARDING FEDERALLY SPONSORED RESEARCH OR DEVELOPMENT

Not applicable to this application.

BACKGROUND

Field

Example embodiments in general relate to a bioelectrical signal controlled exercise machine system for allowing an exerciser to control the state of an exercise machine and exercise environment.

Related Art

Any discussion of the related art throughout the specification should in no way be considered as an admission that such related art is widely known or forms part of common general knowledge in the field. Those skilled in the art will appreciate that exercise machines generally provide for exercisers to change resistance settings based on their strength, size, training objectives, and other conditions unique to each exerciser.

Typically, exercisers use exercise machines for a period of time necessary to realize their workout objectives. For instance, an exerciser may perform ten repetitions of an exercise at one particular weight or resistance setting, then stop the exercise to change the weight or resistance to a different setting, then perform more repetitions of the same exercise at the new weight.

The intermittent cycle of "exercise-stop-exercise" breaks the continuity of the exercise routine, and injects considerable non-exercise time into the duration of the exercise session. This "down-time" during which an exerciser is changing the machine settings is effectively lost. Therefore, an exerciser desiring to exercise for forty-five minutes would necessarily spend more than forty-five minutes for their session in order to account for the down-time. On the other hand, a gym owner looks at exerciser's "down times" as lost profits. When exercisers occupy a machine for a longer period, fewer people are able to use the machine during the course of any given day.

SUMMARY

An example embodiment of the present invention is directed to a bioelectrical signal controlled exercise machine system. The bioelectrical signal controlled exercise machine system includes an exercise machine, a bioelectrical sensor device and a control unit in communication with the bioelectrical sensor device and the exercise machine. The control unit is adapted to receive data from the bioelectrical sensor device relating to measured bioelectrical signals of the human exerciser, and wherein the control unit transmits a control signal to the exercise machine to change the state of the exercise machine based on the data from the bioelectrical sensor device.

At least one embodiment of the present invention is a new and novel system and method providing for an exerciser to set or change their entire exercise experience, and more specifically change one or more elements of the exercise environment by means of transmitting electrical signals generated by one or more electrodes or microphones placed on an exerciser's body.

At least one embodiment of the present invention comprises the use of a plurality of electrodes that sense electrical energy generated by the brain and/or muscles, and transmit the amplified signal to a processor and controller to selectively change two or more elements related to the exercise environment. Additionally, at least one embodiment of the present invention provides for the use of voice commands to control additional elements related to the exercise environment.

The elements of a typical exercise environment, preferably in a gym or similar fitness facility, include the lighting of the facility, the heating or cooling level, music intended to establish an exercise tempo, weight or resistance settings that are continually changed for different exercises, or to accommodate exercisers of different strength levels, and the sequence of exercises that would be performed over the course of the intended exercise period.

One embodiment of the present invention uses two or more electroencephalogram (EEG) electrodes, and/or two or more surface electromyography (EMG) electrodes, and/or a voice-input device, individually or together which sense electrical signal inputs generated on demand by the exerciser, in order to control a multiple of elements of the typical exercise environment as just described.

One embodiment of the present invention is a new and novel method of controlling two or more discrete elements of the exercise environment, input into the system preferably comprises at least discrete input sources though not required. Therefore, the multi-channel input into the controller of the embodiment may be preferably expressed as one of the following:

EEG1 and EEG2=two discrete output control signals.
EMG1 and EMG2=two discrete output control signals.
EEG and MIC (microphone)=two discrete output control signals.

Using the simple formulae just described, a larger number of control signals driving various changes to the exerciser environment may be generated by an expanded formula that may consist of multiple source inputs. For example, control signals (CS) controlling seven different exercise environment variables may rely on sensor inputs consisting of:

EEG1; EEG2; EMG1; EMG2; EMG3; EMG4; MIC1=CS1; CS2; CS3; CS4; CS5; CS6; CS7

An EEG detects electrical activity in the brain using small conductive electrodes in contact with the scalp. Two EEG electrodes are required to read electrical brain activity, the two electrodes comprising one channel. Therefore, an EEG "helmet" or headband worn by the exerciser provides for retaining a multiple of electrodes, and maintains those electrodes in communication with the scalp to thereby generate at least two output channels.

When EEG tests are performed in a clinical environment, for instance, at the neurology department in a hospital, the patient typically lays quietly, without movement, so as not to disrupt the signals. However, in an exercise environment, exercisers are physically active while performing exercises. This high intensity muscle movement generates electromyography signals that can degrade the electroencephalograph signals. Spurious signals that degrade EEG signals are referred to as artifacts.

Artifacts typically encountered in an exercise facility include:
Artifacts with movement of the electrodes—which occurs during exercise,
Artifacts from EMG signals generated by activity of muscles close to EEG electrodes,
Artifacts with ambient 110V power in facility
Artifacts from poor/loss of electrode grounding that can result in spikes of up to 50-60 Hz.

EMG tests for athletes are well known by those skilled in the art. Motor neurons are electrical signals that cause muscles to contract. Therefore, higher value electrical signals are produced by the muscles being contracted. The electrical potential of the muscle membrane ranges from 50 μV, and up to 20 to 30 mV depending on the muscle activated. Similar to EEG signals that are continually generated based on a person's mental and physical activity, EMG signals are inherently generated whenever muscles contract. Also similar to EEG signals, a person can intentionally contract a muscle as a mind-commanded means of generating a specific on-demand electrical signal that can be used to control an event.

Therefore, the embodiment of the present invention as just described further provides for the use of EMG as another mind-initiated, on-demand generator of electrical signals that control specific events while at the same time, allowing the exerciser to continue to exercise. Such events may include for instance, increasing the volume of music playing, or changing the resistance level of an exercise machine.

It is well known to those artisans that all EEG and EMG signals have the potential to degrade as a result of artifacts. It was therefore discovered that the use of more than one type of electrode, and the use of multiple electrodes provided a larger number of data streams that, when analyzed together, help reduce the occurrence or impact of artifacts, and provide a means to validate the mind-controlled signals used to modify the exerciser's environment.

Anticipating a large number of artifacts that could degrade the EEG signal, various embodiments provide for at least one algorithm that incorporates amplification, buffering and low pass filtering of the EEG signal to increase the signal to noise ratio between the EEG and artifact signals, and smoothing of the wave form to normalize out of character data, thereby reducing the influence of artifacts on the desired channel signal.

Various embodiments provide for yet a third method of generating a mind-controlled signal. By means of a throat microphone, the exerciser may elect when to speak, and specifically what word to speak, thereby activating a voice recognition circuit that creates an output signal correlating to one or more words programmed into a voice actuation processor. The voice-actuated control may be used in conjunction with EEG and EMG signals. For instance, an on-demand mind-generated alpha wave may actuate a motor to increase the angle of the exercise plane fro the horizontal. While the exerciser maintains the brain wave level, the motor will continue to increase the exercise angle. By speaking a preprogrammed word, for instance "stop", the exerciser can override the EEG signal and cause the inclination to temporarily stop at the desired angle.

As can be readily appreciated, an exerciser, while exercising, may concentrate on various thought, muscle contraction and/or voice command actuation of one or more control signals, all of the control signals being thought stimulated, to control one or more elements of the exerciser's environment.

More specifically, the various embodiments teach one or more systems that will allow an exerciser to automatically change the various settings on an exercise machine, change music or tempo of sounds listened to during exercise, change the ambient room temperature or change room lighting simply by training their mind to actuate one or more neurobiological or voice sensors As can readily be appreciated, the new and novel method of mind-controlling exercise machine settings allow the exerciser to continue exercising without interruption, and without removing their hands from an exercise machine in order to physically change machine settings or other elements of their exercise environment.

Therefore, one exemplary embodiment of the present invention is system and method providing for an exerciser to control elements of their exercise environment by means of intentionally increasing ionic current within the certain neurons of the brain, the current being sensed by EEG electrodes in contact with the exerciser's scalp.

Another exemplary embodiment of the present invention is system and method providing for an exerciser to control elements of their exercise environment by means of intentionally thinking about, and therefore contracting specific muscles to increase neuromotor electrical signal levels as sensed by EMG electrodes placed in contact with the exerciser's scalp or face.

Another exemplary embodiment of the present invention is system and method providing for an exerciser to control elements of their exercise environment by means of intentionally thinking about, and therefore speaking certain words into a microphone, the words having been preprogrammed to correlate to actuation of a specific output signal that controls one or more elements of their environment.

Another exemplary embodiment of the present invention is a system and method providing for an exerciser to think about, and therefore control elements of their exercise environment without the use of their hands, by means of actuating one or more EMG, EEG and/or microphone sensors worn by the exerciser.

Yet another exemplary embodiment of the present invention is a device worn about the head of an exerciser, the device containing at least a power supply, a plurality of electrodes capable of generating at least two channels of signals, the electrode pairs comprising EEG electrodes, EMG electrodes, a means of amplifying the electrode signals, and a means of transmitting the signals to a signal processor.

Another exemplary embodiment of the present invention is a device worn about the head of an exerciser, the device containing at least a power supply, a microphone, a plurality of electrodes capable of generating at least two channels of signals, the electrode pairs comprising EEG electrodes, EMG electrodes, a means of amplifying the electrode signals, and a means of transmitting the signals to a signal processor.

Yet another exemplary embodiment of the present invention is at least signal conditioning algorithm that processes EEG and/or EMG signals to substantially reduce the detrimental effects of artifacts that are increasingly present when neuromotor and other neurobiological signals are sensed on a rapidly moving exerciser during exercising.

These and other embodiments will become known to one skilled in the art, especially after recognizing the commercial value of exercisers being able to control exercise machine settings and other elements of their exercise environment simply by thinking about changing one or more elements, the control means thereby reducing the total exercise period by eliminating any interruption of their exercise routine to manually change any machine or other settings. The time-savings of the present invention correlate positively to increased profits for the gym facility in which the present invention is implements as a means to control elements of each exerciser's environment. The present invention is not intended to be limited to the disclosed embodiments.

There has thus been outlined, rather broadly, some of the features of the bioelectrical signal controlled exercise machine system in order that the detailed description thereof may be better understood, and in order that the present contribution to the art may be better appreciated. There are additional features of the bioelectrical signal controlled exercise machine system that will be described hereinafter and that will form the subject matter of the claims appended hereto. In this respect, before explaining at least one embodiment of the bioelectrical signal controlled exercise machine system in detail, it is to be understood that the bioelectrical signal controlled exercise machine system is not limited in its application to the details of construction or to the arrangements of the components set forth in the following description or illustrated in the drawings. The bioelectrical signal controlled exercise machine system is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Example embodiments will become more fully understood from the detailed description given herein below and the accompanying drawings, wherein like elements are represented by like reference characters, which are given by way of illustration only and thus are not limitative of the example embodiments herein.

FIG. 1c is a chart illustrating various elements related to an exerciser's environment.

FIG. 2 is an exemplary diagram of a brain wave frequency chart.

FIG. 3 is an exemplary diagram of a representative exerciser wearing an electroencephalograph electrode outfitted headband.

FIG. 8a-8c is an exemplary diagram showing a representative exerciser wearing a throat microphone, and a list of voice command instructions, and a block diagram of a control circuit for adjusting an exercise machine.

DETAILED DESCRIPTION

An example bioelectrical signal controlled exercise machine system generally includes an exercise machine, a bioelectrical sensor device and a control unit in communication with the bioelectrical sensor device and the exercise machine. The control unit is adapted to receive data from the bioelectrical sensor device relating to measured bioelectrical signals of the human exerciser, and wherein the control unit transmits a control signal to the exercise machine to change the state of the exercise machine based on the data from the bioelectrical sensor device.

The phrase "exercise environment" is used herein to mean one or more of any physical element with which an exerciser engages before, during or after exercising on an exercise machine in a gym facility, examples of which include but are not limited to resistance setting, weight setting, attitude of the exercising plane, room temperature, room lighting level, type or volume of music. Audible or visual cues to exercise tempo, and type of exercises and the sequence of exercises performed during a workout session, each of which may be referred to as a environmental "element" without specificity as to which element is being referred to unless a specific element is named.

Control circuits are well known to those skilled in the art. It should be noted that it is not the objective of the embodiments herein to limit the architecture or function of a control system of any particular control system design or method, but rather to broadly describe the applicability of control systems when used to change elements of an exercise environment which may include but not be limited to switches, solenoids, potentiometers, and valves. The broadest interpretation should be given to control systems as they may apply to controlling any element of the exerciser's environment.

Figure 1A:
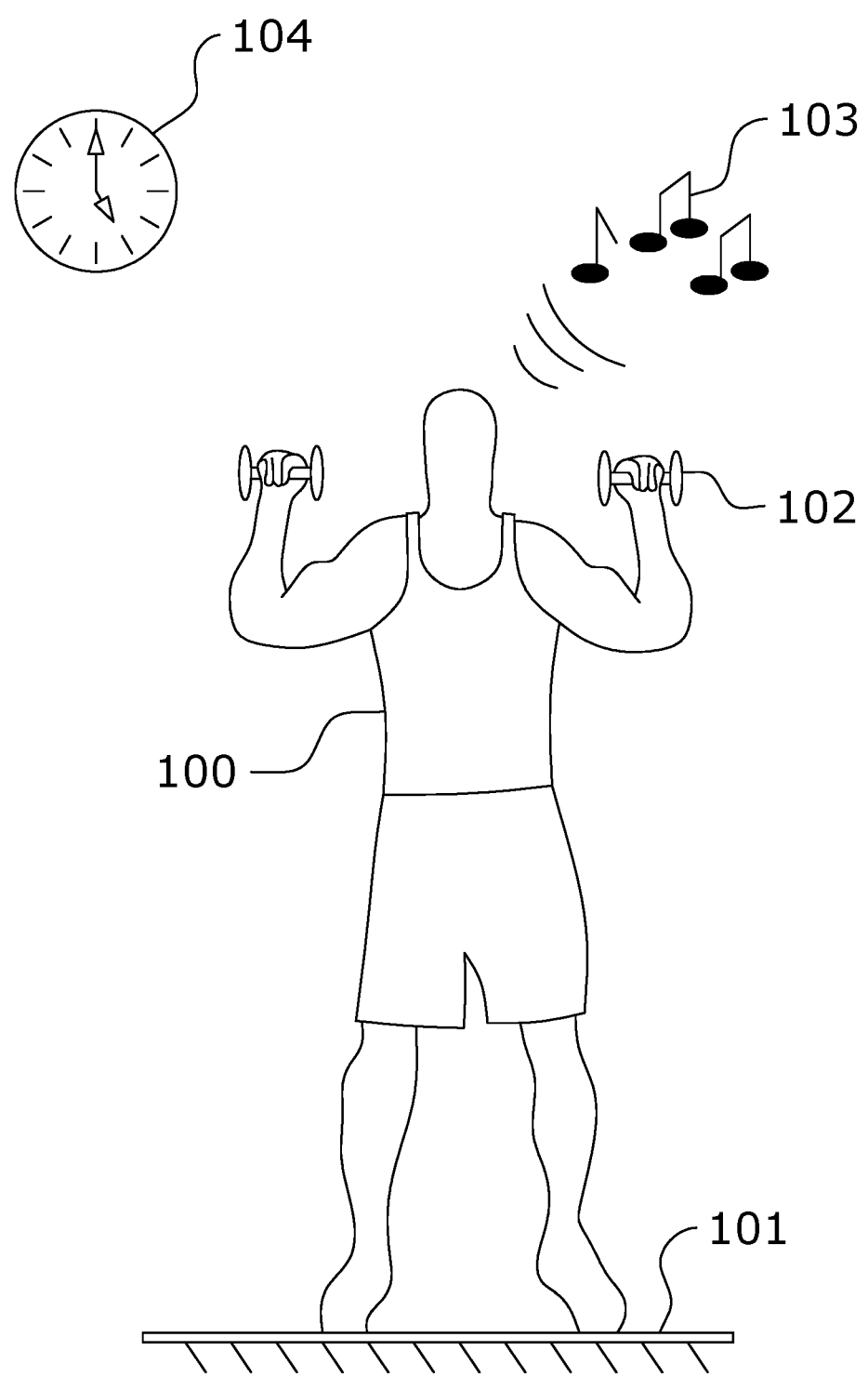
FIG. 1a is a front view of an exerciser on a horizontal surface performing an exercise.
Figure 1B:
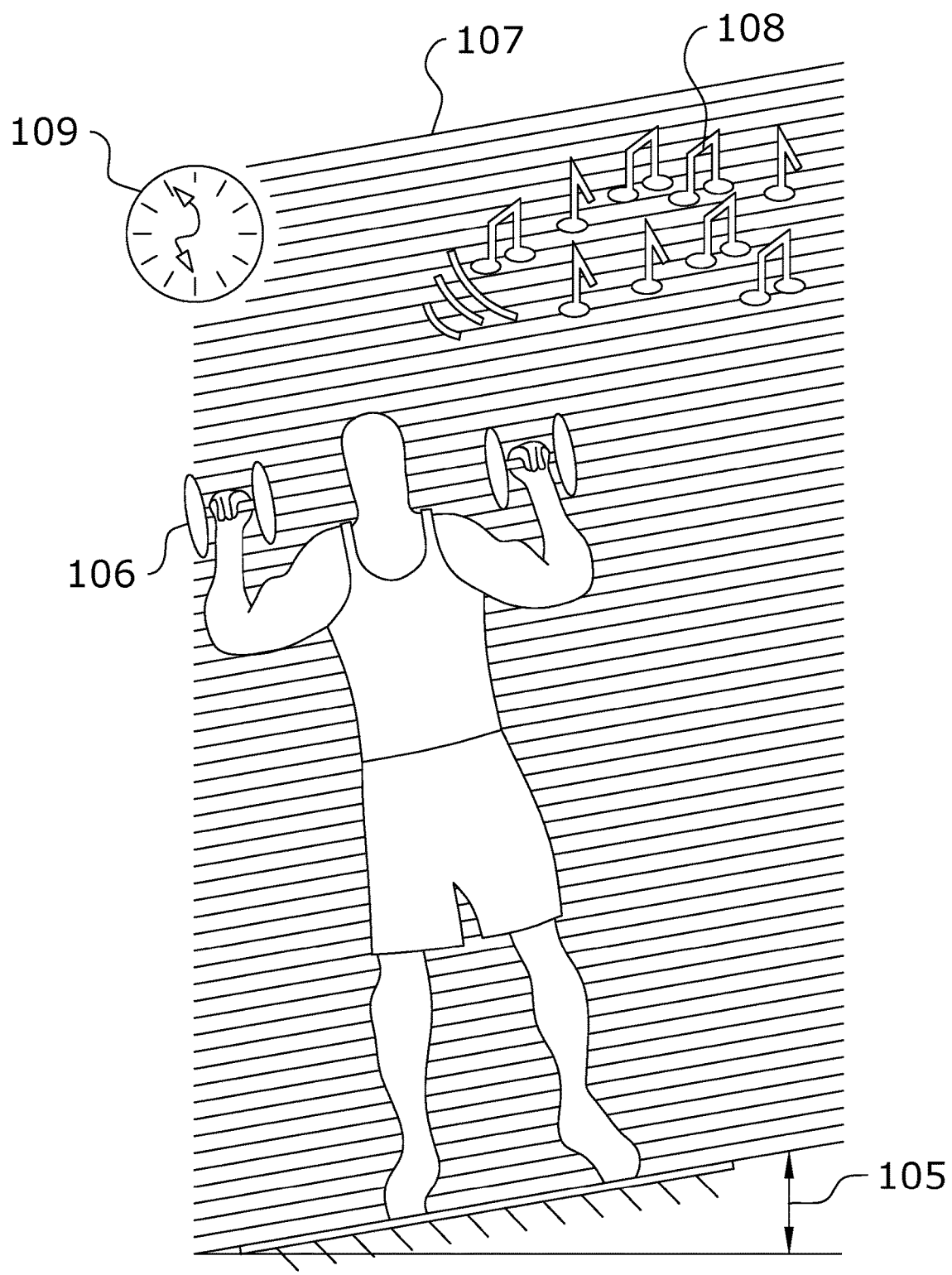
FIG. 1B is a front view of an exerciser on an inclined surface performing an exercise.

FIGS. 1a-1c are exemplary diagrams illustrating various elements related to and exerciser's environment. During the course of a typical exercise routine, exercisers must address various elements of their environment in order to benefit from their workout. Other elements are typically out of the hands of exercisers who must rely on the gym establishment to.

More specifically, a typical exerciser 100 exercises on a substantially horizontal plane 101. During the exercise, the exerciser will select a certain weight 102 that provides a resistance equivalent against which they will exercise muscles. In some environments, the exerciser will hear music 103 that motivates the exerciser or establishes an exercise tempo 104.

One embodiment of the present invention provides for an exerciser to modify the elements of their exercise environment, hands-free, by controlling the elements with their mind. For instance, the exerciser can select a heavier weight 106 by concentrating on an actuation means to change the machine resistance settings. The exerciser may also focus thoughts so that actuators change the substantially horizontal exercise plane to an inclined plane 105, while at the same time providing the exerciser a hands-free means to change the music 108 by actuating a music control circuit. The exerciser may also change the room lighting from bright light, to dimmed light 107, while at the same time allow the exerciser to increase the frequency, and hence tempo 109 of an audible sound.

Although not exhaustive, typical elements encountered in their exercise environment are listed in the exercise environment chart 110. It is preferable that each and every one of these elements be modifiable by an exerciser from time to time during their exercise routine, and especially without having to stop the routine, dismount the exercise machine, make any preferred adjustment, then re-mount and re-start their routine.

FIG. 2 is an exemplary diagram of a brain wave frequency chart. More specifically, healthy human brains generate different brain waves at different frequencies and amplitudes throughout the day, depending on their activity. Electrical signals increase as groups of neurons are accessed to perform a function. Brain wave rhythms are generally accepted to include alpha, beta, gamma, delta and theta waves 200, each with a corresponding frequency range 201, and a fluctuation amplitude 202. As can be readily seen in the chart, the amplitude changes 203 in each of the rhythms correlate to mental activity.

At least one embodiment therefore provides for EEG electrodes to sense, record and transmit brainwave fluctuations that correspond to certain brain activity, the EEG signals ultimately controlling various circuits to change elements of the exerciser's environment. As an exerciser practices mental activity to actuate a control circuit, they become better at controlling changes in brainwave activity upon demand.

For example, an exerciser who wanted to increase the exercise resistance of a machine may focus on changing their alpha and beta wave amplitude in order to actuate a circuit that would change the resistance. If the control circuit is triggered when there is a maximum differential between alpha and beta brainwaves compared to the running normal difference between these rhythms, the exerciser may lower their alpha amplitude by increasing their mental focus and visual interaction with their surroundings, while at the same time increasing beta by exerting mental efforts and visually engaging with their surroundings.

FIG. 3 is an exemplary diagram of a representative exerciser 300 wearing a bioelectrical sensor device 310 to measure electrical signals from the exerciser's body. (e.g. an electroencephalograph electrode outfitted headband). More specifically, one embodiment of a headband of the present invention comprises an adjustable band 301 (e.g. elastic and stretchable such as an elastic headband), one first EEG electrode 302, one second EEG electrode 303, one ear clip electrode 305, and a power supply and signal transmission means 304.

During exercise, at least two electrodes record and transmit to a computer EEG signals related to neuron activity proximal to the electrodes. The two electrodes create a single channel for communicating the signal to a computer via a wireless communication means. Although a single channel comprises two electrodes, a headband providing for a plurality of electrodes that output at least two channels is preferred.

Many different types of EEG headbands or helmets are known to those skilled in the art, many of which are cumbersome, require a laborious setup protocol, and many of which are hard wired to a receiving computer. However, many of these types of EEG helmets or sensors are not conducive for use in an exercise environment. It is preferred that the exerciser, who is highly mobile when exercising, wear an EEG headband that is light weight, provides for the minimum number of electrodes required to control the desired number of circuits, and that is in wireless communication with the system controller.

Figure 4:
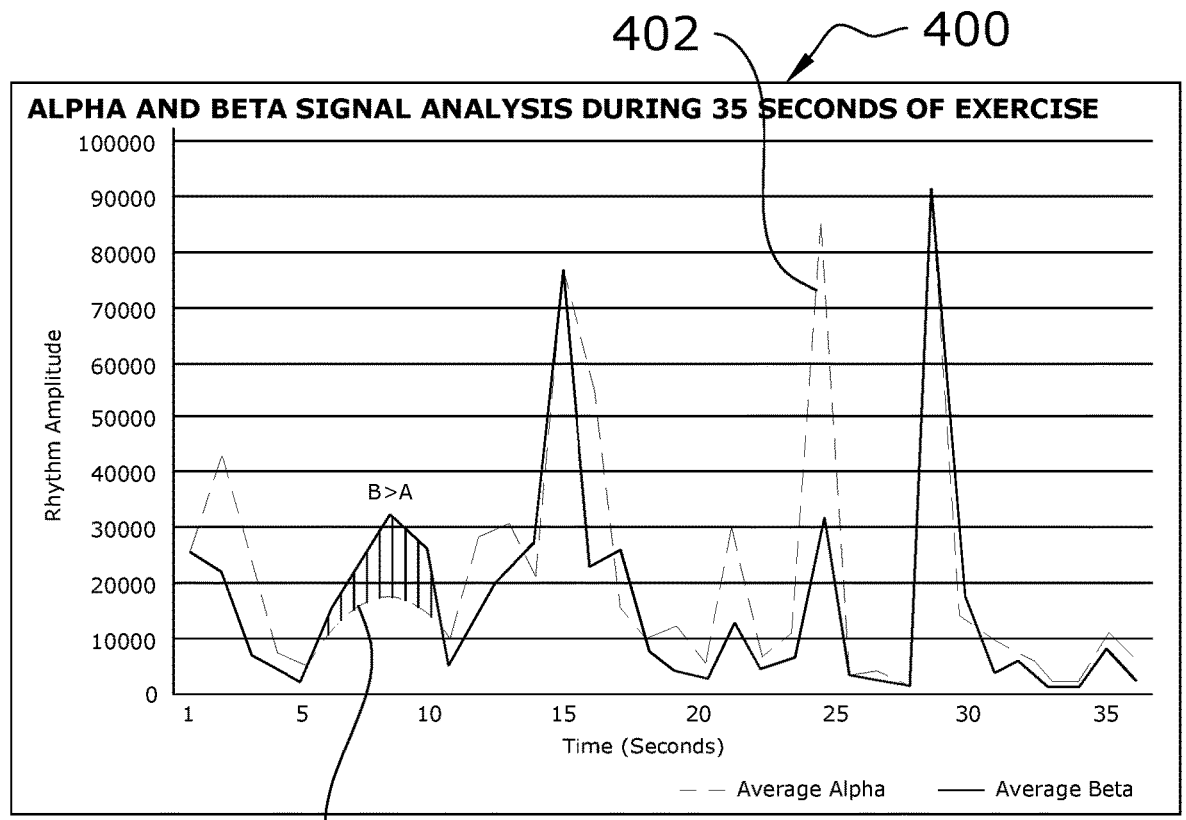
FIG. 4 is an exemplary diagram illustrating differences in brainwave frequency response during exercise.

FIG. 4 is an exemplary diagram illustrating differences in brainwave frequency response during exercise. More specifically, the chart 400 displays actual EEG signals that were obtained through testing on an exerciser wearing a light weight, wireless EEG headband as previously described. During exercise, the amplitude of the alpha and beta waves were independently recorded. In many cases, it can be seen that the amplitude changes of the two rhythms were very similar. In one instance, 402, the amplitude of the average alpha far exceeded the amplitude of the beta at the same point in time during the test. This differential occurred within approximately two seconds, and may be attributed to an artifact.

More importantly, while alpha generally exceeded beta in amplitude, a condition occurred wherein the exerciser maintained a significant amplitude increase in beta relative to alpha 401. The duration of this condition exceeded five seconds, illustrating a consciousness on the part of the exerciser to focus on intensifying beta activity. One embodiment of the invention recognizes this preferred condition for a predetermined minimum time duration, activates a circuit that controls the change in one element of the exerciser's environment.

Figure 5:
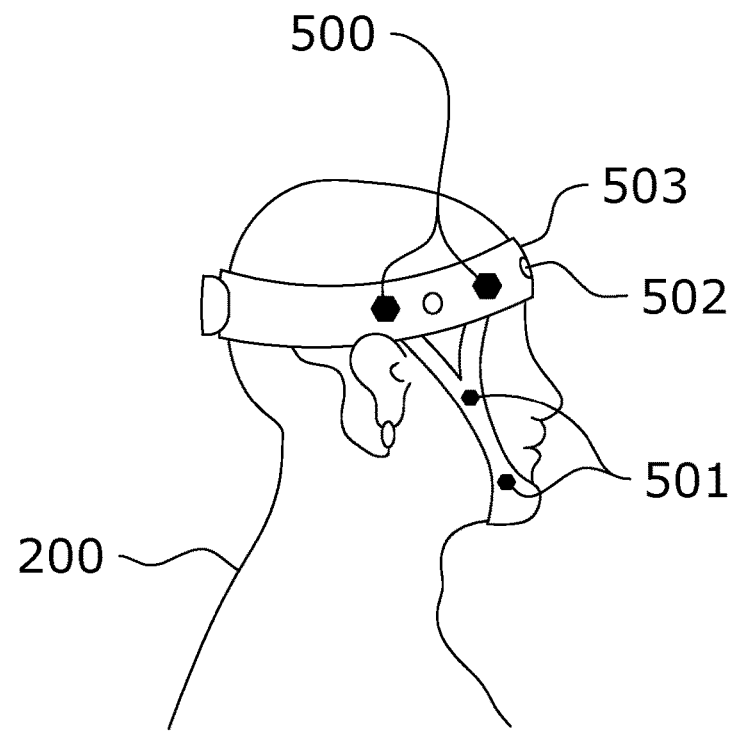
FIG. 5 is an exemplary diagram of a representative exerciser wearing an electroencephalograph and electromyography electrode outfitted headband.

FIG. 5 is an exemplary diagram of a representative exerciser 200 wearing an electroencephalograph and electromyography electrode outfitted headband 503. It can be readily seen that the headband provides for multiple channel outputs that, correspondingly, control multiple elements of the exerciser's environment by generating thought-activated signals. The headband comprises at least two EEG electrodes 202, and at least two EMG electrodes 500. It is well known that EMG electrodes record neuromuscular electrical signal activity of the muscles proximal to the electrodes. As a means to provide for more than one EMG channel, a chin strap comprising at least two EMG electrodes 501 placed proximal to mandibular and temporal muscles allow for the exerciser to increase electrical signal levels, and therefore control specific control circuits by intentionally focusing thoughts on activating the targeted muscles by flexing their chin, of clenching their teeth. In practice, data received from all of the electrodes is amplified and transmitted wirelessly in real time from the headband to a receiver and controller.

Therefore, the headband and chin strap comprising multiple EEG and EMG electrodes provides for an exerciser to thoughtfully actuate a plurality of control circuits during exercising, each control circuit thereby preferably controlling one of multiple elements in their environment. U.S. Pat. No. 8,812,075 to Neurosky, Inc. discloses an exemplary sensor headset suitable for use with the various embodiments of the present invention and is hereby incorporated by reference herein. U.S. Publication No. 2014/01487,15 filed by Neurosky, Inc. discloses various types of biosensors that are suitable for use with the various embodiments of the present invention and is also hereby incorporated by reference herein.

Figure 6:
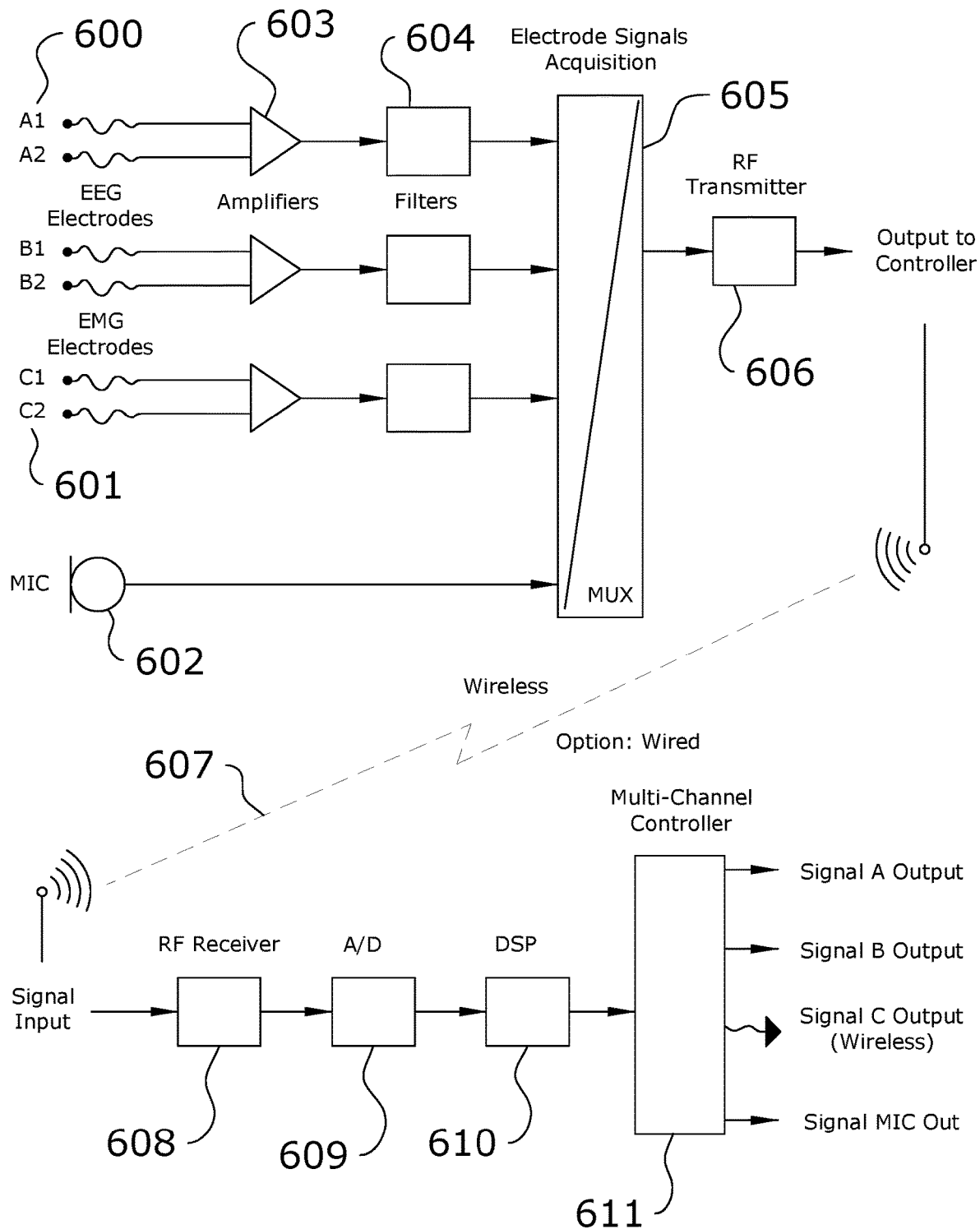
FIG. 6 is an exemplary diagram showing a multi-channel mind controlled exercise machine adjustment system.

FIG. 6 is an exemplary diagram showing a multi-channel mind controlled exercise machine adjustment system. A headband as previously described provides for a plurality of sensors including two channels of EEG electrodes 600, electrodes for one EMG channel 601, and an audio sensor device 602 (e.g. a throat microphone 602). It should be noted that the configuration of input sensors is not meant to be limiting, and any number of any combination of any of the sensors just described may be used in a multi-channel mind controlled exercise machine.

An exerciser may actuate each or all of a plurality of channels by focusing one or more thoughts toward generating increased electrical activity in the brain, in muscles by intentionally stimulating one or more muscles, and/or by consciously considering a particular voice command correlating to controlling a specific desired element of their exercise environment.

Amplifiers 603 provide for increasing the signal strength of the neurobiological signals detected by the electrodes. Further, filters, such as low pass or high pass filters provide for scrubbing artifacts from the electrode-input electrodes. Depending on the brain wave rhythm preferred for processing as a mind controllable signal, the high pass or low pass filters, and in some cases both filter ranges will be used to attenuate the artifacts. Filters are preferably used to clean the signal from EMG electrodes as well, the filters being selected based on the frequencies of the desired and non-desired ranges.

The amplifiers and filters just described may be integrated into EEG and EMG electrode modules, and may not be discrete components through which the neurobiological signals pass. Those skilled in the art will appreciate that microphone circuits are well known, and any recognized circuit may be used for receiving and communicating a voice input to a signal acquisition module 605 preferably affixed to the headband. The acquisition module further provides for multiplexing a plurality of EEG, EMG and mic signals, all of the signals together being transmitted to a controller module by means of an RF transmitter 606. The RF signals may be transmitted to the controller by communication wire, but are preferably communicated via a wireless communication link 607.

An RF Receiver circuit 608 receives the multiplexed signal. An analog to digital circuit 609 converts the signals to digital format for processing by a digital signal processor 610. The process of receiving, converting and processing analog signals is not meant to be limiting. The large body of art is well known, and any recognized receiving, converting and processing circuit may be used without no effect on the intended function of the various embodiments of the present invention.

A multi-channel controller 611 provides for processing each of the received signals to activate a specific circuit that will control its respective element. In practice, and merely for example, a first EEG channel A may be used to actuate a motor to increase the angle of an exercise platform, while a second EEG channel B is used to increase the music volume of the exercise music. A third channel C from EMG electrodes may be used to increase the resistance setting of the exercise machine. Each of the channels just described would be actuated by various means practiced by the exerciser, including placing their mind is a meditative state with eyes closed in order to increase alpha amplitude relative to beta, the predetermined differential being achieved thereby triggers the respective output control signal. A second condition wherein the exerciser opens their eyes and focuses on the machine element, and strongly visualizes a change in machine attitude increases the beta signal amplitude relative to the alpha, the predetermined differential being achieved thereby triggers its respective output control channel.

In both of the just described cases, once the intentional thought process actuates the control output signal, for instance, a motor that turns on to elevate the exercise machine, the switch could remain open until the exerciser speaks a control word "stop" into a microphone, the word having been preprogrammed to terminate any EEG or EMG originated control signal.

Although many variations of the system of controlling a plurality of control signals that modify one or more elements of the exerciser's environment may be used without deviating from the purposed function of controlling signals using mind-originated thoughts, and the headband and/or variations of the headband previously described by rely on one or more channels generated by EEG, EMG and/or mic signals, independently or in combination with one another, to describe every possible configuration and circuit design would be burdensome, but would nevertheless illustrate the broad application of the new and novel method of exercisers being able to mind control many elements within their exercise environment, hands-free, and on demand during the course of their exercising.

Figure 7:
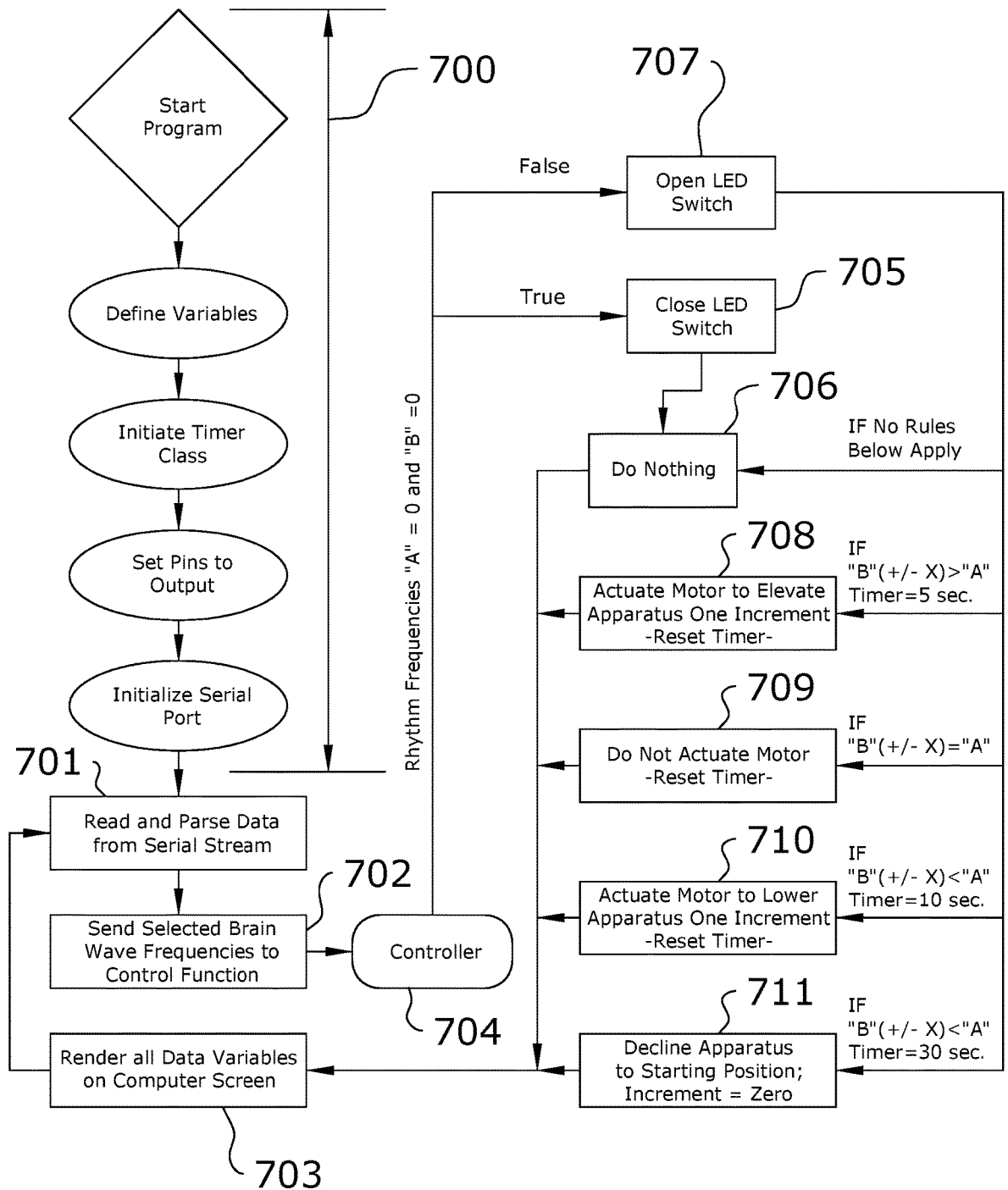
FIG. 7 is an exemplary diagram showing one system and method of translating EEG signals into control circuits to adjust an exercise machine.

FIG. 7 is an exemplary diagram showing one system and method of translating EEG signals into a control circuit to adjust an exercise machine. A software program for a control circuit is launched 700 wherein brainwave signal input variables are defined, time periods during which the brainwave signal must be received to create a result, and terminal contacts for a serial port output are defined.

Not shown, a headband with at least two EEG electrodes is affixed to an exerciser, and is powered on so that neurobiological electrical signals are sensed by the electrodes. Signals received by the electrodes are communicated to the control circuit 701 and parsed into the various rhythms including alpha, beta, gamma, theta and delta, all of which are characterized by different frequencies. The selected frequencies being defined in the setup 700 establish the rhythms that will be used by the controller 704 to control the machine function.

Presented as one example, alpha "A" and beta "B" frequencies are used in the illustration. The electrode-sensed signal amplitude changes of the A and B frequencies are monitored over time, with normalization of the signal by the controller to compute a running average of the amplitude changes as a means of smoothing what are oftentimes highly erratic signal changes. The smoothed data stream thereby becomes a more reliable data source upon which to apply control function rules.

At the start of the exemplary exercise, an exerciser is positioned on an exercise machine positioned on a substantially horizontal plane. Various rules, having been previously established, provide for signal conditions that correlate to controller function. For instance, a first rule establishes a T/F gate that compares amplitude changes of A and B frequencies. If A does not equal B, an switch 707 is opened to allow for machine control. If A equals B, the switch is closed 705 and a "null" control event 706 will be triggered.

A positive result from one rule 708 will cause the controller to actuate a motor that inclines an exercise platform. This rule requires the exerciser to establish and maintain for at least 5 seconds a condition where the amplitude change of B (plus an error margin) is greater than the amplitude change of A. As one method discovered during experimentation, an exerciser may achieve this condition while exercising by staring intensely at one end of the machine, and visualizing that end of the machine being elevated by the motor. This mental exercise is just one proven example of how to reduce the amplitude of the alpha frequency, while elevating the amplitude of the beta frequency. A positive result from another rule 709 means that the amplitude changes of A and B are substantially equal, indicating that no control signal is desired by the exerciser. The control circuit defaults to a "null" status and ne event is triggered.

Yet another rule 710 is established so that an exerciser can reverse the inclination of the exercise machine. More specifically, if the amplitude of the B frequency is less than the amplitude of the A frequency for a period of not less than 10 seconds, the inclined machine will begin to decline to a new position of one "increment". An increment may be defined as a 5-degree incline or decline, but the actual increment amount is irrelevant, and any preprogrammed increment may be used. As one method discovered during experimentation, an exerciser may achieve this condition while exercising by closing their eyes and meditating on the wind-down of one exercise, relaxing and reducing overall muscle activity prior to starting the next exercise in a sequence of exercises. This mental exercise is just one proven example of how to reduce the amplitude of the beta frequency, while elevating the amplitude of the alpha frequency.

A final rule 711 is used to anticipate the end of an exercise routine by concluding that the reduction in muscle activity, and the eyes-closed meditation condition is persisting for more than 30 seconds. As a result of a positive result of this rule, the inclined exercise machine begins to return to its horizontal starting point, readying for exerciser dismount.

As can be seen, the exerciser, through the use of mental imaging, is able to increase or decrease the incline of an exercise machine. It should be noted that machine incline is but one of many elements of an exercise environment, and the control signals and rules of the immediately preceding example may be modified to apply to controlling an element other than machine incline or decline.

Figure 8C:
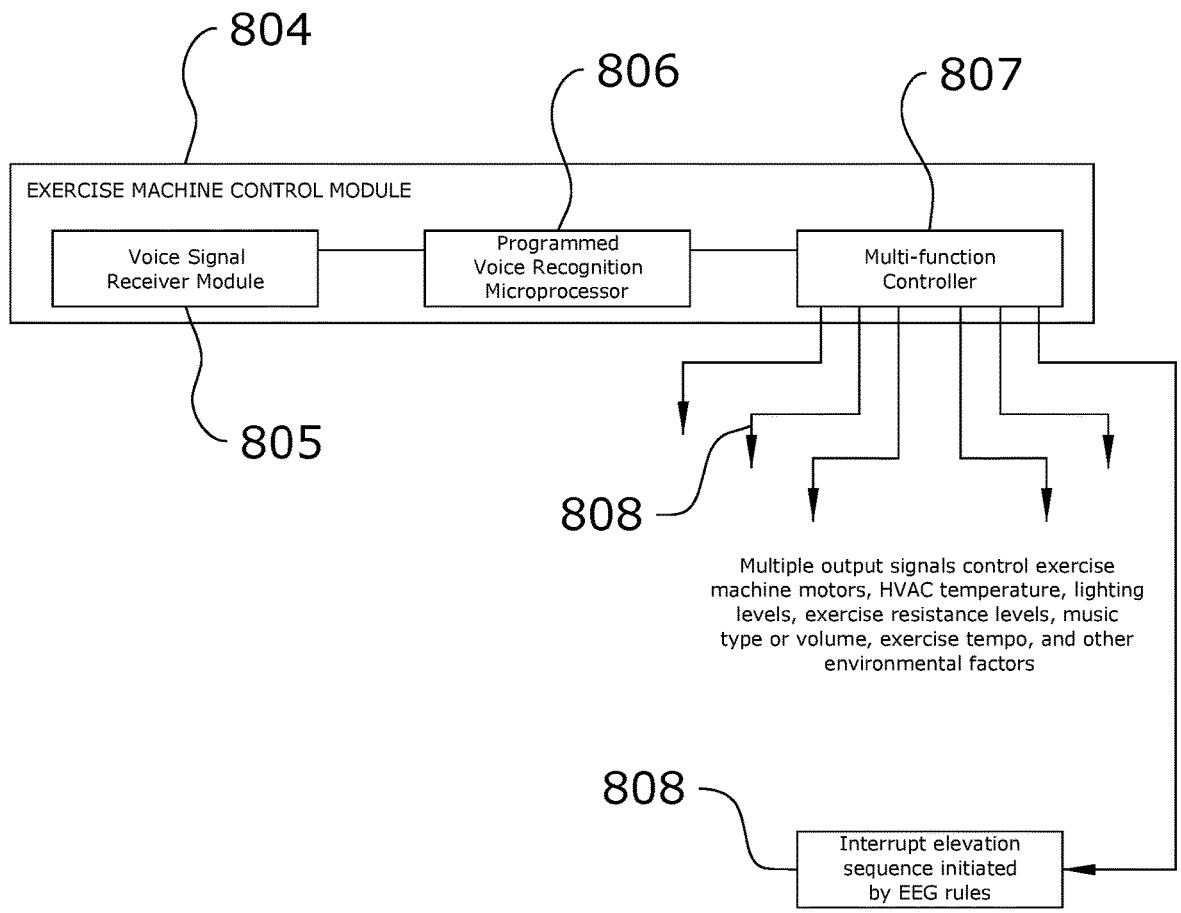

FIGS. 8a-8c are exemplary diagrams showing a representative exerciser wearing a throat microphone, and a list of voice command instructions, and a block diagram of a control circuit for adjusting an exercise machine.

As another means of controlling elements if an exercise environment, an exerciser 200 is shown with a band 800 affixed to the neck. A microphone 801 is retained by the band, securing the microphone against the skin proximal to the vocal cords. Throat microphones are well known by those skilled in the art, and are frequently used as a hands-free communication means.

Used separately, or in conjunction with an EEG and/or EMG headband, the throat microphone provides for an exerciser to thoughtfully consider what element of their environment that prefer to change, and remembering a series of word or phrase commands 802 can actuate a controller function via a voice recognition circuit not shown. A list of controller functions 803 is shown but is not intended to be limiting. Any element of the exercise environment may be controlled by a voice command separately or in conjunction with EEG and/or EMG input.

As one example of a voice recognition module activating multiple controller output signals, a control module 804 is installed on an exercise machine not shown. The microphone is in wireless communication with a voice signal receiver module 805 that incorporates an A/D conversion circuit, a preprogrammed processor 806 containing a list of recognized words and the associated instruction that are communicated to a multi-function controller 807.

Six controller output signals 808 are shown, but ten or more output signals are possible, each controlling a different element of the exerciser's environment. The number of controller output signals is limited only by reason of the number of elements desired to be controlled. It is preferable, however, that the controller 807 processes only one input request at a time, with a reasonable delay prior to initiating the next command in a string of voice commands.

As one illustration of the use of mind-initiated voice control in conjunction with mind-initiated EEG controls, the exerciser, having initiated the elevation sequence by meeting the B>A EEG rule (FIG. 7, 708) desires to stop the elevation actuator prior to the elevation reaching a predetermined increment. By initiating a voice command, for example "stop elevation". As shown in the drawing, the command sends an interrupt instruction 808 to the elevation controller, thereby providing the exerciser with multiple method of mind-controlling the machine elevation element of their exercise environment.

As will be appreciated by those skilled in the art, providing exercisers with the ability to mind-control a plurality of elements within their exercise environment allow exercisers to continue exercising without interruption while changing any element desired. The increased efficiency and mind-machine engagement reduces the overall workout time by eliminating the traditional start-stop sequence required whenever an exerciser changes a machine setting. Further, they will appreciate that the reduced exercise time provides for a gym facility to conduct more exercise classes within any given period of daily operation, thereby creating more operating revenue and profit.

Any and all headings are for convenience only and have no limiting effect. Unless otherwise defined, all technical and scientific terms used herein have the same meaning as commonly understood by one of ordinary skill in the art to which this invention belongs. Although specific terms are employed herein, they are used in a generic and descriptive sense only and not for purposes of limitation. All publications, patent applications, patents, and other references mentioned herein are incorporated by reference in their entirety to the extent allowed by applicable law and regulations.

The data structures and code described in this detailed description are typically stored on a computer readable storage medium, which may be any device or medium that can store code and/or data for use by a computer system. This includes, but is not limited to, magnetic and optical storage devices such as disk drives, magnetic tape, CDs (compact discs), DVDs (digital video discs), and computer instruction signals embodied in a transmission medium (with or without a carrier wave upon which the signals are modulated). For example, the transmission medium may include a telecommunications network, such as the Internet.

Figure 9:
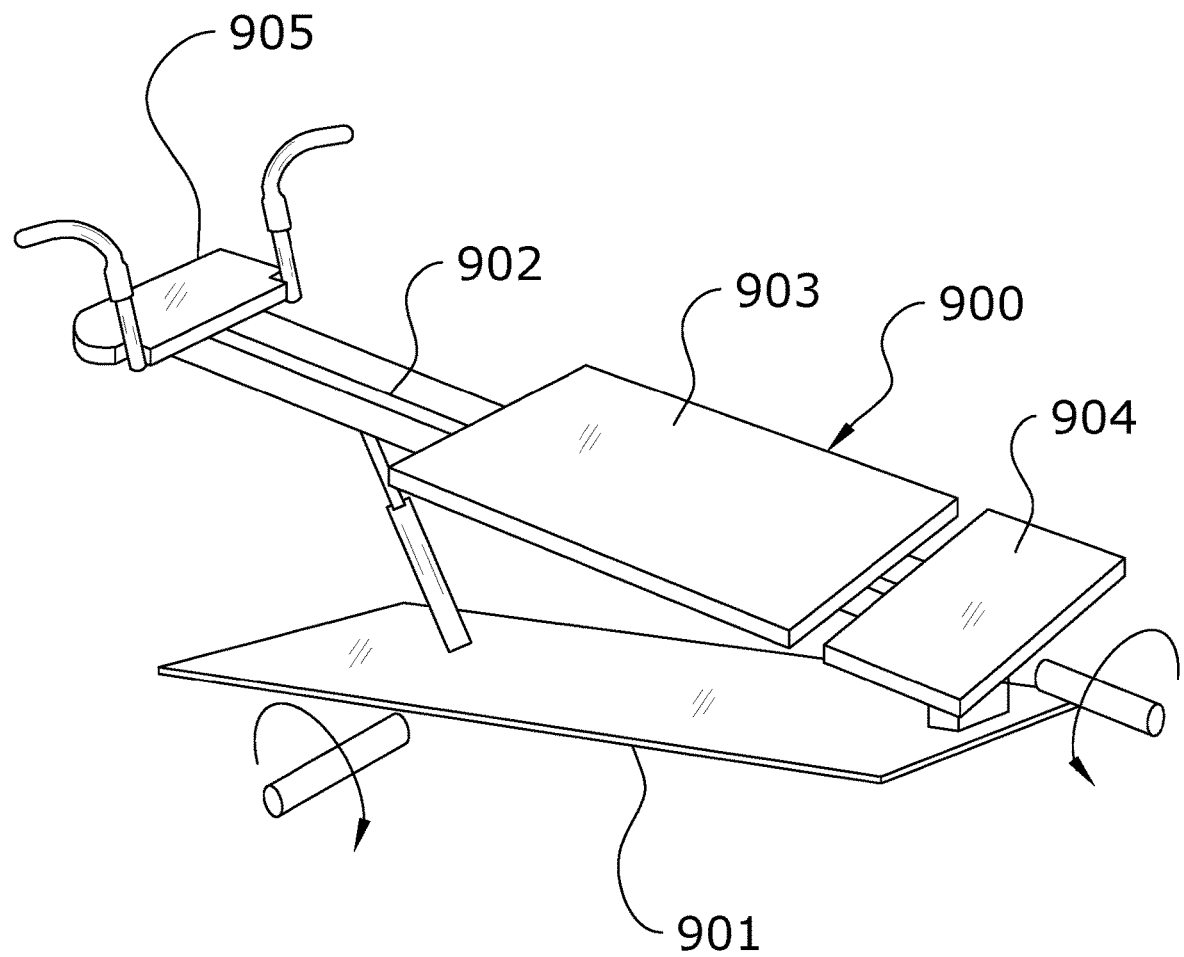
FIG. 9 is an upper perspective view of an exemplary exercise machine with a movable carriage.
Figure 10:
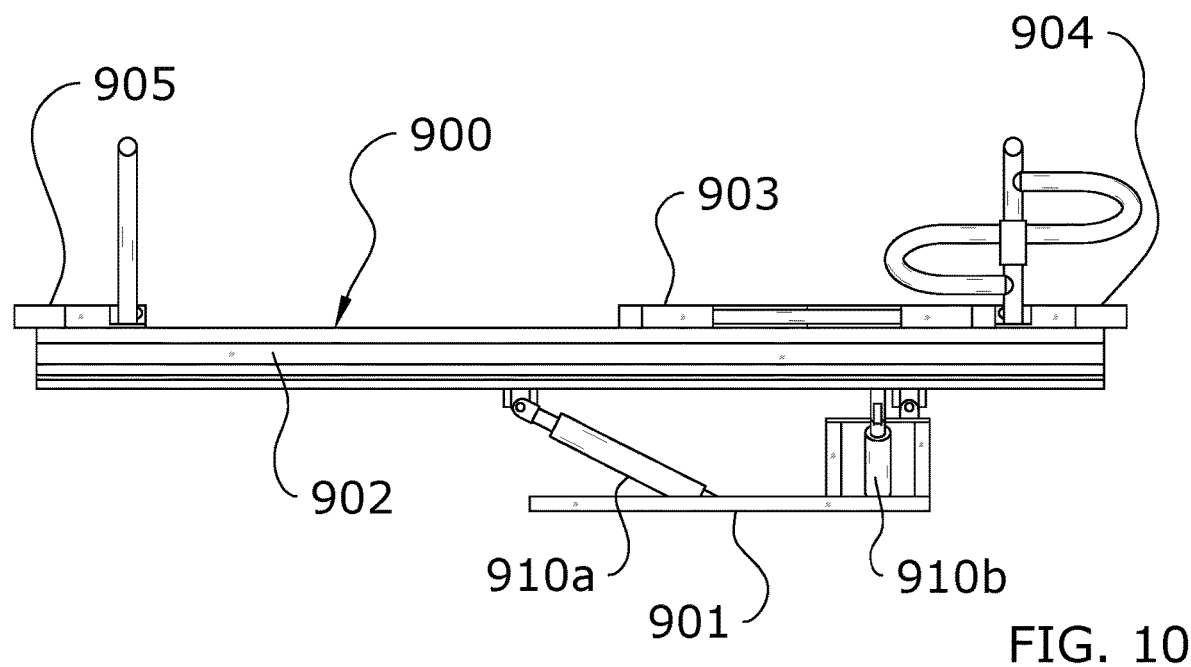
FIG. 10 is a side view of an exemplary exercise machine in a horizontal state.
Figure 11:
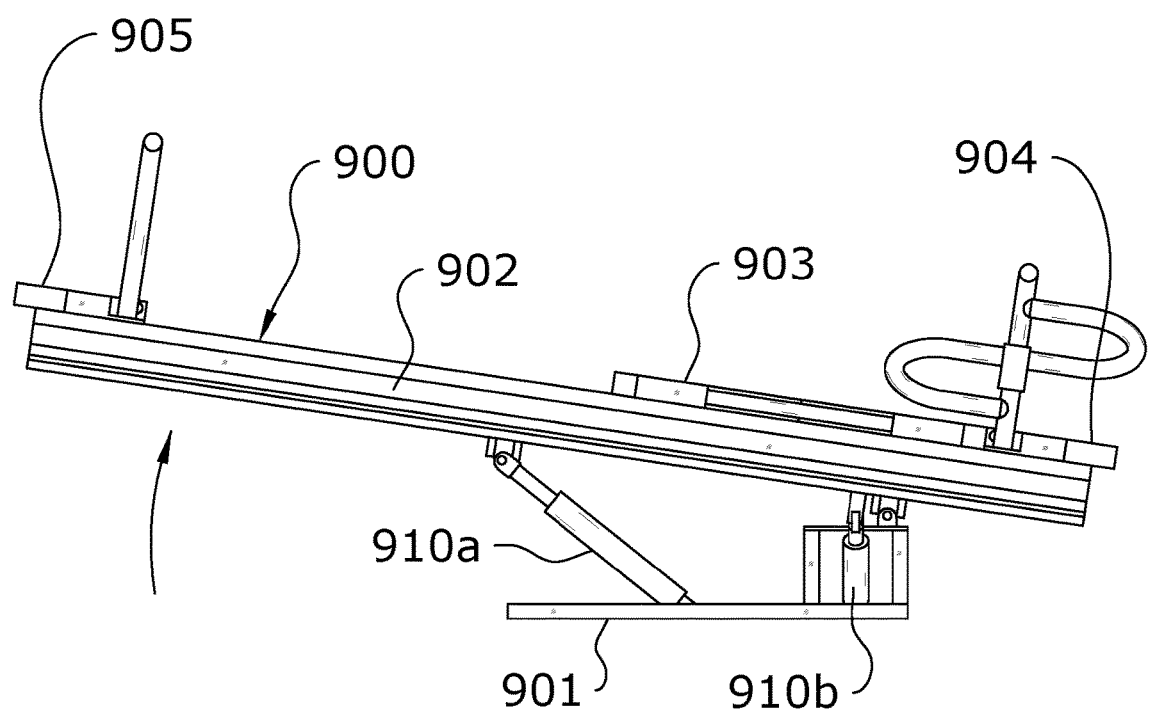
FIG. 11 is a side view of an exemplary exercise machine in an inclined state.
Figure 12:
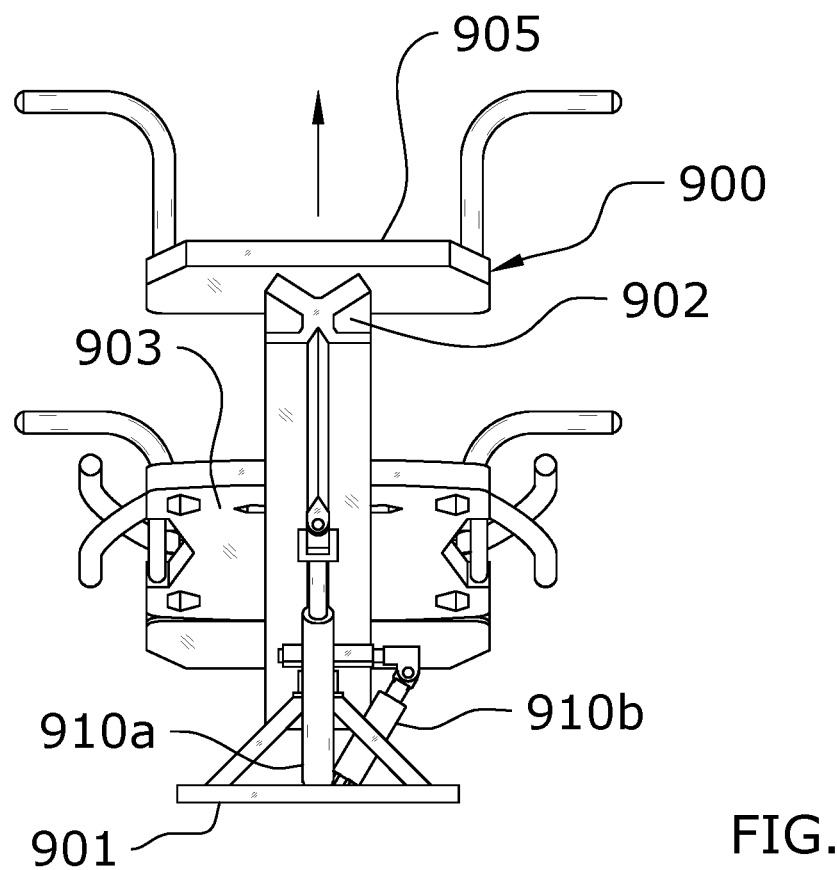
FIG. 12 is a front view of an exemplary exercise machine in an inclined state.
Figure 13:
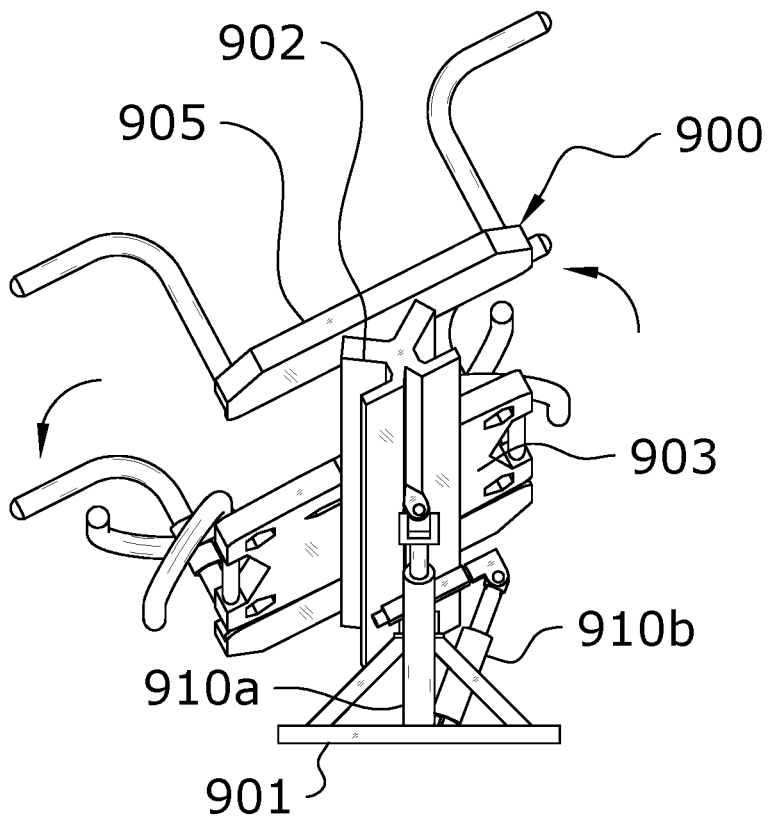
FIG. 13 is a front view of an exemplary exercise machine in an inclined state and rotated to the side about the roll axis.
Figure 14:
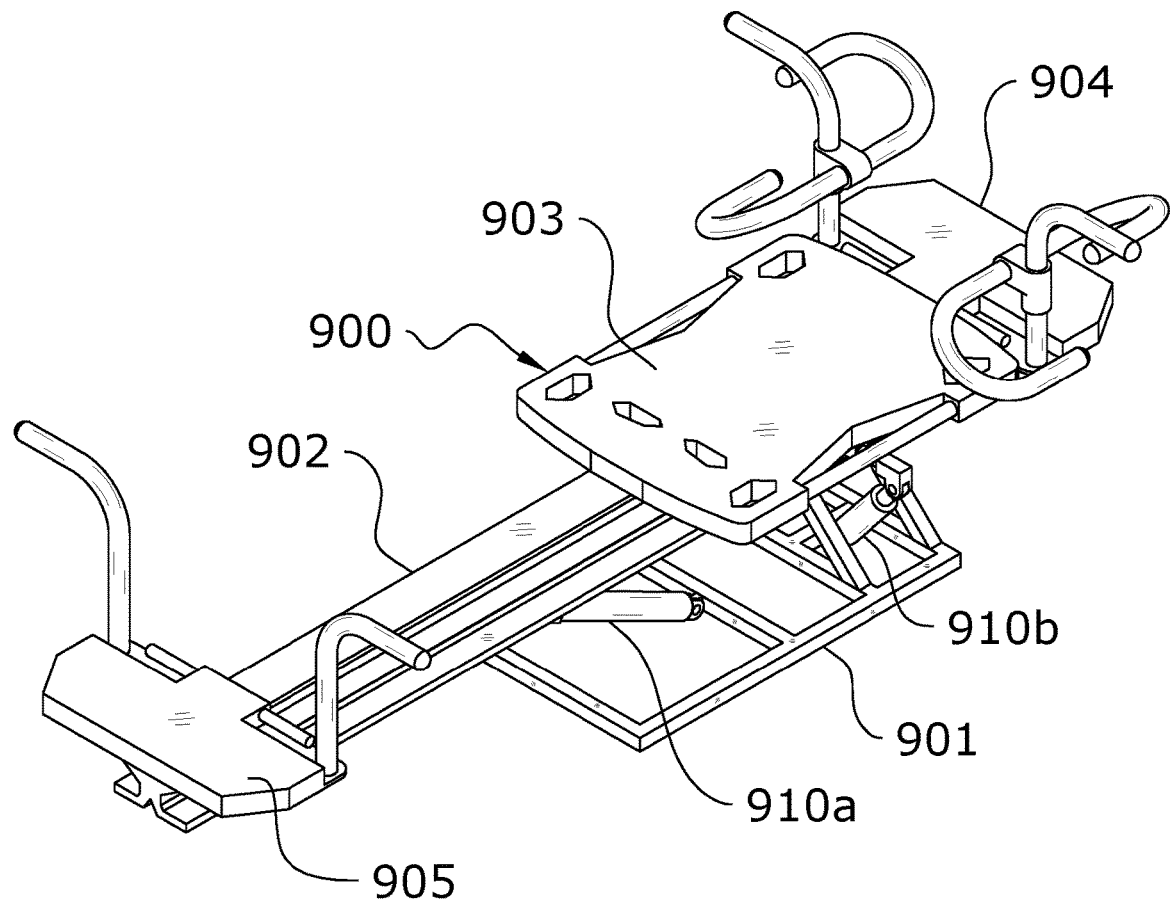
FIG. 14 is an upper perspective view of an exemplary exercise machine that is adapted to pivot and/or roll.
Figure 15:
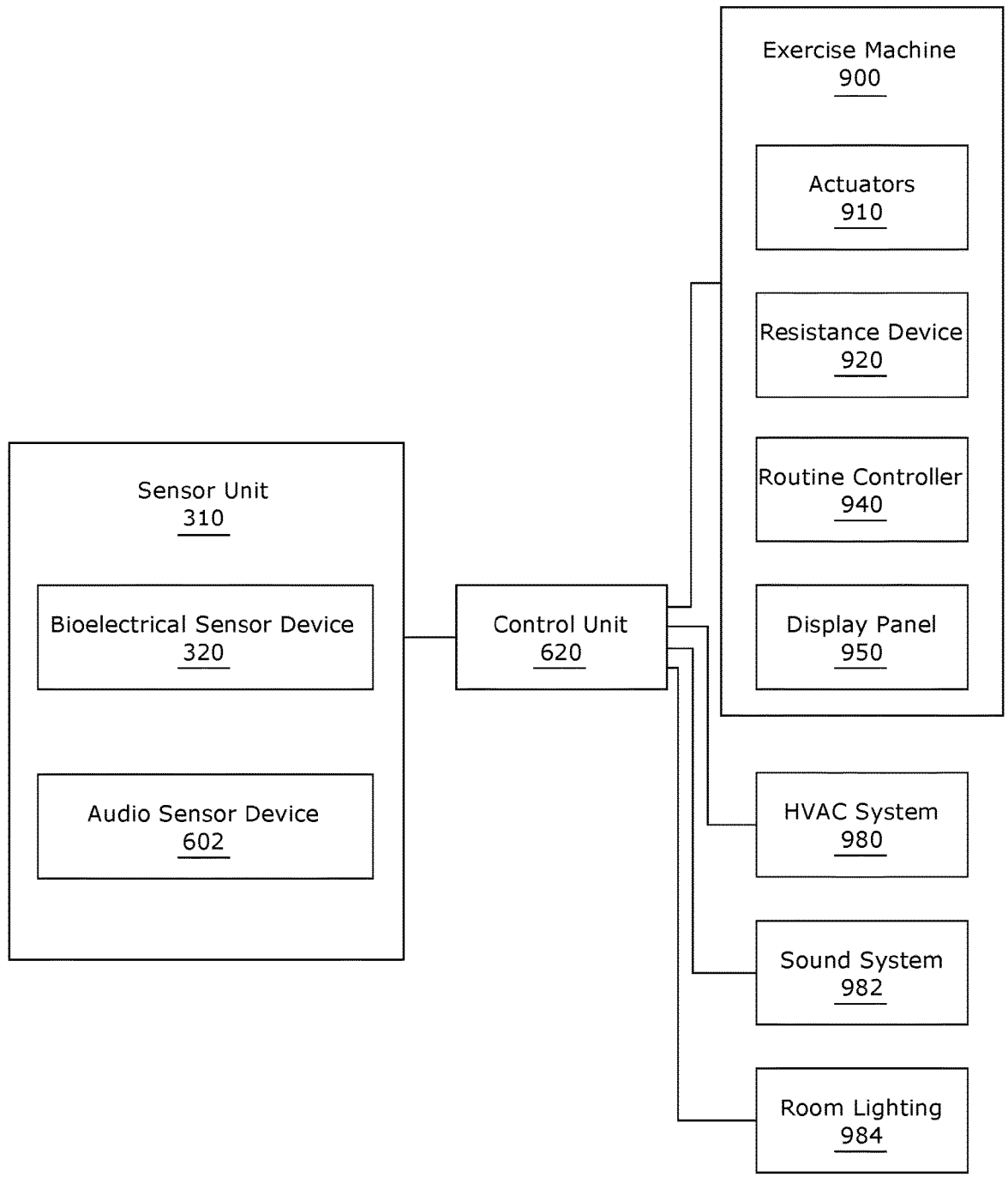
FIG. 15 is a block diagram illustrating the communications between the sensor unit, the control unit, the exercise machine and various environmental systems.

The exercise machine 900 preferably includes at least one actuator 910 as illustrated in FIG. 9 of the drawings. The actuator is adapted to change a state of the exercise machine 900. The state of the exercise machine 900 may be comprised of various aspects such as, but not limited to, attitude (pitch, roll and/or yaw of the exercise machine 900), a resistance level of the exercise machine, the amount of weight for the exercise machine to be lifted, the temp of the exercise machine, the workout routine for the exercise machine and various other controllable states for an exercise machine.

The exercise machine may be comprised of any type of exercise machine known or developed in the future that has a state that is adjustable that can be controlled. For example, the exercise machine may be comprised of a Pilates exercise machine, a treadmill, elliptical machine, rowing machine, weight lifting machine and the like. As shown in FIGS. 9 through 14 of the drawings, the exercise machine 900 is may be comprised of a base 901, at least one rail 902 movably supported above the base 901, a carriage 903 movably positioned on the rail 902 in a slidable manner, and one or more actuators 910 connected between the frame of the exercise machine and the rail 902 to adjust the attitude of the rail (e.g. one or more actuators 910a may be used to adjust the pitch of the exercise machine and one or more actuators 910b may be used to adjust the roll of the exercise machine). The actuators 910, 910a, 910b may be comprised of any actuator device capable of moving the exercise machine such as, but not limited to, electric actuators, hydraulic actuators, motorized actuators, motors, rotating motors, linear actuators and the like. The actuators 910, 910a, 910b may extend and retract to move the exercise machine 900 and/or the actuators 910, 910a, 910b may rotate to move the exercise machine 900.

The carriage 903 is adapted to move in a reciprocating manner on the rail 902. Though not shown, the exercise machine may include two or more rails. The movable carriage preferably is connected to a resistance device 920 (e.g. springs, elastic bands, electronically controlled resistance device, etc.) that adjusts the level of resistance to the carriage in at least one direction of movement of the carriage. The resistance device 920 is adapted to provide a resistance force at a resistance level to the carriage during an exercise. The resistance device is further connected to the frame of the exercise machine such as the rail, base or other structure that the carriage moves relative to. U.S. Publication No. US-2015-0360083-A1 to Lagree discloses an Exercise Machine Adjustable Resistance System and Method suitable for use with the various embodiments and is hereby incorporated by reference herein. The exercise machine 900 may also include a display panel 950 to display various types of exercise related information to the exerciser (e.g. resistance level, pitch level, roll level, time remaining in the workout, the amount of time worked out, the exercise routine, biometric information, bioelectric measurements by the bioelectrical sensor device 320. The exercise machine may also include a routine controller 940 which controls the current exercise routine for the exercise machine 900 which may adjust the various states of the exercise machine to perform different types of exercises (e.g. adjustment of the pitch, roll, yaw, resistance and other adjustable features of the exercise machine 900).

U.S. Patent Pub. No. US-2015-0343250-A1 filed by Lagree discloses a Multi-Axis Adjustable Exercise Machine suitable for usage with the various embodiments of the present invention and is hereby incorporated by reference herein. U.S. Pat. No. 7,803,095 to Lagree discloses another Exercise Machine suitable for usage with the various embodiments of the present invention and is hereby incorporated by reference herein.

The various embodiments of the present invention use a sensor unit 310 that preferably uses a bioelectrical sensor device 320 that is adapted to detect a bioelectrical signal of a human exerciser before, during and after the performance of an exercise. The bioelectrical sensor device 320 includes one or more of each of the following types of biosensors: an electroencephalography (EEG) sensor, and an electromyography (EMG) sensor. The bioelectrical sensor device 320 is adapted to communicate with the control unit by wired or wireless communication. The sensor unit 310 may also include an audio sensor device 602 that is in communication with the control unit 620 and is adapted to receive audio commands from the human exerciser as illustrated in FIG. 8b of the drawings.

A control unit 620 is in communication with the bioelectrical sensor device and the exercise machine (wirelessly and/or wired communications). The control unit 620 is adapted to receive data from the bioelectrical sensor device 320 (and audio sensor device 602) relating to measured bioelectrical signals of the human exerciser. The control unit 620 transmits a control signal to the exercise machine 900 to change the state of the exercise machine based on the data from the bioelectrical sensor device 320 to perform the desired function by the exerciser. The control unit 620 controls the actuators 910, 910a, 910b of the exercise machine to control the pitch, roll and/or yaw of the exercise machine (or any combination thereof). The control unit 620 further can control the resistance level provided to the carriage by the resistance device 920.

In addition, the control unit 620 may transmit a control signal to various other environmental systems in the building where the exerciser is performing an exercise such as, but not limited to, the HVAC system 980 (to control temperature and climate conditions), the sound system 982 (to control volume and the type of music playing during the workout) and room lighting 984 (to control the level and type of lighting in the room).

To use the various embodiments of the present invention, the bioelectrical sensor device 320 and/or audio sensor device 602 are physically connected to the human exerciser. The exerciser performs an exercise on the carriage 903 of the exercise machine 900. The bioelectrical sensor device 320 detects one or more bioelectrical signals of the human exerciser which are used by the control unit 620 to calculate and determine how to control the exercise machine 900 (e.g. lift, lower, roll to the right, roll to the left, increase resistance, lower resistance) and/or various environmental elements (e.g. lighting, room temperature, song choice, music level). The control unit 620 transmits the appropriate control signal(s) to the exercise machine and/or various environmental elements based on the detected bioelectrical signal(s). For example, the control signal adjusts a state of the actuator 910, 910a, 910b to correspondingly adjust the attitude of the exercise machine (e.g. pitch, roll and/or yaw).

At least one embodiment of the bioelectrical signal controlled exercise machine system is described above with reference to block and flow diagrams of systems, methods, apparatuses, and/or computer program products according to example embodiments of the invention. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments of the invention. These computer-executable program instructions may be loaded onto a general-purpose computer, a special-purpose computer, a processor, or other programmable data processing apparatus to produce a particular machine, such that the instructions that execute on the computer, processor, or other programmable data processing apparatus create means for implementing one or more functions specified in the flow diagram block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, embodiments of the invention may provide for a computer program product, comprising a computer usable medium having a computer-readable program code or program instructions embodied therein, said computer-readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks. Accordingly, blocks of the block diagrams and flow diagrams support combinations of means for performing the specified functions, combinations of elements or steps for performing the specified functions, and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special-purpose hardware and computer instructions.

The present invention may be embodied in other specific forms without departing from the spirit or essential attributes thereof, and it is therefore desired that the present embodiment be considered in all respects as illustrative and not restrictive. Many modifications and other embodiments of the bioelectrical signal controlled exercise machine system will come to mind to one skilled in the art to which this invention pertains and having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although methods and materials similar to or equivalent to those described herein can be used in the practice or testing of the bioelectrical signal controlled exercise machine system, suitable methods and materials are described above. Thus, the bioelectrical signal controlled exercise machine system is not intended to be limited to the embodiments shown, but is to be accorded the widest scope consistent with the principles and features disclosed herein.

What is claimed is:

1. A bioelectrical signal controlled exercise machine system, comprising:
    an exercise machine;
    an electroencephalography (EEG) sensor, wherein the electroencephalography (EEG) sensor is configured to record brain waves generated by a brain of a human exerciser, wherein the brain waves measured by the electroencephalography (EEG) sensor are comprised of an alpha wave and a beta wave, and wherein the electroencephalography (EEG) sensor is configured to transmit an EEG signal comprising an alpha wave amplitude and a beta wave amplitude; and
    a control unit in communication with the electroencephalography (EEG) sensor and the exercise machine, wherein the control unit is configured to receive the EEG signal from the electroencephalography (EEG) sensor, wherein the control unit determines a control signal based on the alpha wave amplitude relative to the beta wave amplitude and vice versa, and wherein the control unit adjusts a state of the exercise machine based on the control signal when the alpha wave amplitude is greater or less than the beta wave amplitude and vice versa.

2. The bioelectrical signal controlled exercise machine system of claim 1, wherein the exercise machine comprises a carriage movably positioned on a rail, wherein the carriage is configured to move in a reciprocating manner on the rail.

3. The bioelectrical signal controlled exercise machine system of claim 2, wherein the exercise machine includes a resistance device connected to the carriage, wherein the resistance device is configured to provide a resistance force at a resistance level to the carriage during an exercise, and wherein the state of the exercise machine comprises the resistance level and the control unit adjusts the resistance level by controlling the resistance device.

4. The bioelectrical signal controlled exercise machine system of claim 1, wherein the state of the exercise machine comprises a resistance level of the exercise machine.

5. The bioelectrical signal controlled exercise machine system of claim 1, wherein the control unit is in communication with an HVAC system to control a temperature.

6. The bioelectrical signal controlled exercise machine system of claim 1, wherein the control unit is in communication with a sound system to control a volume of the sound system.

7. The bioelectrical signal controlled exercise machine system of claim 1, wherein the control unit is in communication with a room lighting to control a level of lighting in a room.

8. The bioelectrical signal controlled exercise machine system of claim 1, further comprising an acquisition module;
    wherein the acquisition module is configured to multiplex bioelectrical signals received from the electroencephalography (EEG) sensor and an electromyography (EMG) sensor; and
    wherein the control unit is configured to receive multiplexed data from the acquisition module.

9. A bioelectrical signal controlled exercise machine system, comprising:
    an exercise machine;
    an electroencephalography (EEG) sensor;
    wherein the electroencephalography (EEG) sensor is configured to measure brainwave signals generated by a brain of a human exerciser, wherein the brainwave signals measured by the electroencephalography (EEG) sensor are comprised of an alpha wave and a beta wave; and
    a control unit in communication with the electroencephalography (EEG) sensor configured to:
        receive data from the electroencephalography (EEG) sensor relating to the brainwave signals of the human exerciser comprising an alpha wave amplitude and a beta wave amplitude;
        translate the brainwave signals into a control signal based on the alpha wave amplitude relative to the beta wave amplitude and vice versa; and
        control the exercise machine in accordance with the control signal to adjust a state of the exercise machine when the alpha wave amplitude is greater or less than the beta wave amplitude and vice versa.

10. The bioelectrical signal controlled exercise machine system of claim 9, wherein the exercise machine comprises a carriage movably positioned on a rail, wherein the carriage is configured to move in a reciprocating manner on the rail.

11. The bioelectrical signal controlled exercise machine system of claim 10, wherein the exercise machine includes a resistance device connected to the carriage, wherein the resistance device is configured to provide a resistance force at a resistance level to the carriage during an exercise, and wherein the state of the exercise machine comprises the resistance level and the control unit adjusts the resistance level by controlling the resistance device.

12. The bioelectrical signal controlled exercise machine system of claim 9, wherein the state of the exercise machine comprises a resistance level of the exercise machine.

13. The bioelectrical signal controlled exercise machine system of claim 9, wherein the control unit is in communication with an HVAC system and is configured to control a temperature of the HVAC system.

14. The bioelectrical signal controlled exercise machine system of claim 9, wherein the control unit is in communication with a sound system and is configured to control a volume of the sound system.

15. The bioelectrical signal controlled exercise machine system of claim 9, wherein the control unit is in communication with a room lighting and is configured to control a level of lighting in a room.

16. The bioelectrical signal controlled exercise machine system of claim 9, further comprising an acquisition module;
   wherein the acquisition module is configured to multiplex bioelectrical signals received from the electroencephalography (EEG) sensor and an electromyography (EMG) sensor; and
   wherein the control unit is configured to receive multiplexed data from the acquisition module.

17. A bioelectrical signal controlled exercise machine system, comprising:
   an exercise machine having a resistance device, wherein the resistance device is configured to apply a resistance force;
   an electroencephalography (EEG) sensor, wherein the electroencephalography (EEG) sensor is configured to record brain waves generated by a brain of a human exerciser, wherein the brain waves measured by the electroencephalography (EEG) sensor are comprised of an alpha wave and a beta wave, and wherein the electroencephalography (EEG) sensor is configured to transmit an EEG signal comprising an alpha wave amplitude and a beta wave amplitude; and
   a control unit in communication with the electroencephalography (EEG) sensor and the exercise machine, wherein the control unit is configured to receive the EEG signal from the electroencephalography (EEG) sensor, wherein the control unit determines a control signal based on the alpha wave amplitude relative to the beta wave amplitude and vice versa, and wherein the control unit controls the resistance device of the exercise machine based on the control signal when the alpha wave amplitude is greater or less than the beta wave amplitude and vice versa.

18. The bioelectrical signal controlled exercise machine system of claim 17, wherein the exercise machine comprises a carriage movably positioned on a rail, wherein the carriage is configured to move in a reciprocating manner on the rail, wherein the resistance device is configured to apply the resistance force at a resistance level to the carriage during an exercise.

19. The bioelectrical signal controlled exercise machine system of claim 17, wherein the control unit is in communication with an HVAC system, a sound system or a room lighting.

20. The bioelectrical signal controlled exercise machine system of claim 17, further comprising an acquisition module;
   wherein the acquisition module is configured to multiplex bioelectrical signals received from the electroencephalography (EEG) sensor and an electromyography (EMG) sensor; and
   wherein the control unit is configured to receive multiplexed data from the acquisition module.

* * * * *